(12) United States Patent
Brueser et al.

(10) Patent No.: US 11,486,846 B2
(45) Date of Patent: Nov. 1, 2022

(54) METHOD AND DEVICE FOR ANALYZING A GAS

(71) Applicant: Robert Bosch GmbH, Stuttgart (DE)

(72) Inventors: Christoph Brueser, Reutlingen (DE); Maria Martinez Prada, Aidlingen (DE); Philipp Nolte, Gerlingen (DE); Thomas Claus, Leipzig (DE)

(73) Assignee: Robert Bosch GmbH, Stuttgart (DE)

( * ) Notice: Subject to any disclaimer, the term of this patent is extended or adjusted under 35 U.S.C. 154(b) by 318 days.

(21) Appl. No.: 16/643,706

(22) PCT Filed: Aug. 20, 2018

(86) PCT No.: PCT/EP2018/072401
§ 371 (c)(1),
(2) Date: Mar. 2, 2020

(87) PCT Pub. No.: WO2019/048221
PCT Pub. Date: Mar. 14, 2019

(65) Prior Publication Data
US 2020/0209176 A1 Jul. 2, 2020

(30) Foreign Application Priority Data
Sep. 5, 2017 (DE) .......................... 102017215529.9

(51) Int. Cl.
*G01N 27/14* (2006.01)
*G01N 27/12* (2006.01)
*G01N 33/00* (2006.01)

(52) U.S. Cl.
CPC .......... *G01N 27/14* (2013.01); *G01N 27/124* (2013.01); *G01N 33/004* (2013.01); *G01N 33/0044* (2013.01); *G01N 33/0047* (2013.01)

(58) Field of Classification Search
CPC ...... G01N 27/12; G01N 27/14; G01N 27/124; G01N 33/004; G01N 33/0044; G01N 33/0047
See application file for complete search history.

(56) References Cited

U.S. PATENT DOCUMENTS

2016/0084786 A1    3/2016  Suzuki
2016/0349201 A1   12/2016  Graunke

FOREIGN PATENT DOCUMENTS

DE         19911867 A1    10/2000
DE      102005009246 A1     9/2006
(Continued)

OTHER PUBLICATIONS

International Search Report dated Nov. 27, 2018 of the corresponding International Application PCT/EP2018/072401 filed Aug. 20, 2018.
(Continued)

*Primary Examiner* — Benjamin R Schmitt
(74) *Attorney, Agent, or Firm* — Norton Rose Fulbright US LLP; Gerard Messina

(57) ABSTRACT

A method for analyzing a gas, where a sensitive metal oxide-containing layer is exposed to the gas, includes: reducing the temperature of the sensitive layer from a first temperature to a second temperature, the temperature of the sensitive layer being maintained essentially at the second temperature for a predetermined time period; increasing the temperature of the sensitive layer to a third temperature; measuring at least one electrical resistance value of the sensitive layer while the sensitive layer exhibits essentially the third temperature; and analyzing components of the gas based on the measured at least one electrical resistance value.

10 Claims, 2 Drawing Sheets

(56) References Cited

FOREIGN PATENT DOCUMENTS

| | | |
|---|---|---|
| DE | 102008005821 A1 | 8/2009 |
| DE | 102013212485 A1 | 12/2014 |
| JP | 2016188832 A | 11/2016 |
| WO | 2015121312 A1 | 8/2015 |
| WO | 2018188941 A1 | 10/2018 |

OTHER PUBLICATIONS

Yoshikawa A K et al. "Temperature-dependent dynamic response enables the qualification and quantification of gases by a single sensor," Sensors and Actuators B: Chemical: International Journal Devoted to Research and Development of Physical and Chemical Transducers, Elservier BV, NL. Bd. 40, Nr. 1, 1. May 1997, pp. 33-37.

METHOD AND DEVICE FOR ANALYZING A GAS

CROSS-REFERENCE TO RELATED APPLICATIONS

The present application is the national stage of International Pat. App. No. PCT/EP2018/072401 filed Aug. 20, 2018, and claims priority under 35 U.S.C. § 119 to DE 10 2017 215 529.9, filed in the Federal Republic of Germany on Sep. 5, 2017, the content of each of which are incorporated herein by reference in their entireties.

FIELD OF THE INVENTION

The present invention relates to a method for analyzing a gas and to a device for analyzing a gas. The present invention relates, in particular, to a method and a device for detecting sulfurous substances, volatile organic substances, or carbon monoxide. Such a detection can be used for analyzing ambient air or also breathing air, for example, for recognizing halitosis, smoker's breath, or ethanol in the breath.

BACKGROUND

Electrical semiconductors having metal oxides change their electrical conductivity as a function of the composition of the surrounding gases. Thus, particular chemical compounds can be deposited by adsorption on the semiconductors, thereby altering the conductivity of the semiconductors. By measuring the conductivity or the resistance, it is possible in this way to deduce the substances in the surrounding gas. A sensor is known by way of example from DE 10 2005 009246 A1, where the electrical charge is utilized and evaluated as a measure for the concentration of oxidable or reducible gases or vapors present in the surrounding atmosphere of the sensor.

SUMMARY OF THE INVENTION

Example embodiments of the present invention are directed to a method and a device for analyzing a gas. According to a first aspect, a method for analyzing a gas, where a metal oxide-containing sensitive layer is exposed to the gas, includes reducing the temperature of the sensitive layer from a first temperature to a second temperature, the temperature of the sensitive layer being maintained for a predefined time period essentially at the second temperature; increasing the temperature of the sensitive layer to a third temperature; measuring at least one electrical resistance value of the sensitive layer while the gas exhibits essentially the third temperature; and analyzing components of the gas based on the measured at least one electrical resistance value.

According to a second aspect, a device for analyzing a gas includes an oxide-containing, sensitive layer that is exposable to the gas; a heating unit that is designed to reduce a temperature of the sensitive layer from a first temperature to a second temperature, to maintain the temperature of the sensitive layer for a predefined time period essentially at the second temperature, and to subsequently increase the temperature of the sensitive layer to a third temperature; a measuring device that is designed to measure at least one electrical resistance value of the sensitive layer while the sensitive layer exhibits essentially the third temperature; and an analysis device that is designed to analyze components of the gas based on the measured at least one electrical resistance value.

According to an example embodiment of the present invention, at least two temperature transitions of the metal oxide-containing sensitive layer take place, each of which has an influence on the electrical resistance of the sensitive layer. For this purpose, the sensitive layer is preferably initially heated to the first temperature. The first temperature is selected in such a way that the sensitive layer is freed of adsorbates or adsorbed gases potentially still present. For example, desorption of adsorbate can occur, i.e., decay of near-surface chemical compounds that can have originated, for example, via the contact of a sulfurous gas with the metal oxide surface. The sensitive layer is heated to the first temperature preferably for a predefined time period that is selected to be sufficiently long so that a balance between desorption and adsorption occurs. A well-defined initial state can thus be set. While the temperature of the sensitive layer is reduced to the second temperature, a renewed adsorption of components in the gas on the sensitive layer takes place. The adsorption is a function of the concentration and of the composition of the gas that is located in the surroundings of the sensitive layer during this phase. As the temperature of the sensitive layer is increased again to the third temperature, the desorption described above again takes place that influences, in particular, the electrical conductivity and, as a result, the electrical resistance of the sensitive layer. The present invention is based on the finding that the qualitative change of the electrical resistance as well as of the exact chronological profile of the change of the electrical resistance is a function of both the type of the adsorbates as well as of the concentration of the adsorbates. Thus, it is possible, based on the electrical resistance values, to ascertain particular components of the gas. The degree of adsorption is a function, in particular, of the time period during which the temperature of the sensitive layer is maintained essentially at the second temperature.

The measurement of the resistance at a high temperature is advantageous as opposed to the measurement of the resistance at a lower temperature. Thus, it is possible in general to distinguish the largest possible electrical resistance to be measured from the lowest possible resistance to be measured by a factor of 100 up to 1000 for metal oxide-containing sensors at various temperatures and at various gas atmospheres. The resistance assumes in general significantly higher values at the second lower temperature than at the first and third temperatures that correspond to the usual sensor temperatures. When merely one measurement of the electrical resistance value at the higher third temperature is necessary, no additional complicated measuring electronics for low temperatures and correspondingly high resistance ranges are required. As a result, the device according to the present invention is suitable, in particular, for cost-efficient microcontrollers or ASICs in mobile devices such as smartphones.

According to an example embodiment of the method, the temperature of the sensitive layer is maintained for a predefined time period essentially at the third temperature during the measurement of the at least one electrical resistance value. At a fixed temperature, the chronological profile of the resistance follows a particular curve or kinetics that can be compared with corresponding reference curves. The reference curves can be created for various concentrations or for various compositions of corresponding components of a test gas under the same external conditions, i.e., with the same chronological sequence of the first, second, and third temperatures. Corresponding measured values can be stored in a characteristic diagram.

According to an example embodiment of the method, a chronological profile of the electrical resistance is ascertained. The analysis of the components of the gas is further carried out based on the chronological profile of the electrical resistance. A chronological profile of the gradients of the electrical resistance, in particular, can be ascertained and taken into consideration for determining components of the gas.

According to an example embodiment of the method, the presence and/or the concentration of sulfur compounds, organic compounds, and/or carbon monoxide are ascertained based on the chronological profile of the electrical resistance. Sulfur compounds can include, in particular, odor-causing substances, such as hydrogen sulfide $H_2S$, methane thiol, dimethyl sulfide, and dimethyl disulfide. The organic compounds can include, in particular, volatile compounds, such as alcohol, for example, ethanol.

According to an example embodiment of the method, at least one resistance value of the sensor element is also ascertained while the sensitive layer exhibits the first temperature. The analysis of the components of the gas is further carried out using a comparison of the at least one resistance value at the first temperature with at least one resistance value at the third temperature. The differences in the measured values result from a desorption not yet fully completed at the third temperature.

According to an example embodiment of the method, the first temperature is essentially as high as the third temperature. This simplifies, in particular, the comparison of measured values while the sensitive layer assumes the first temperature and while the sensitive layer assumes the third temperature. Potential differences in resistance values originate not from the temperature differences, but solely from the desorption not yet fully completed.

According to an example embodiment of the method, a time required for the temperature change is negligible with respect to the predefined time period during which the sensitive layer is maintained essentially at the second temperature and/or to the predefined time period during which the sensitive layer is maintained essentially at the third temperature. The time can be negligible if the time is shorter by a factor of 10, 100, or 1000 than the correspondingly predefined time period, during which the sensitive layer is maintained essentially at a constant temperature.

According to an example embodiment of the method, the ascertainment of the at least one electrical resistance value of the sensitive layer takes place in a time period of between 2 milliseconds and 2 seconds after the temperature of the sensitive layer is increased to the third temperature, preferably in a short time period which is less than 30 milliseconds after the increase. The exact time period can, however, be a function of the measuring electronics. In these time ranges, adsorption and desorption have normally not yet reached an equilibrium, so that the ascertained resistance values allow for conclusions to be drawn about the type and concentration of the components of the gas. More generally, the detection of the measured values is set in such a way that, on the one hand, the resistance values are not ascertained too late, since in this case a strengthening effect can no longer be observed, since the substance is already decomposed or desorbed. On the other hand, the resistance values should not be ascertained too soon, since the metal oxide should have reached a temperature that is above a minimum temperature for the desorption.

According to an example embodiment of the method, the first temperature and/or the third temperature are/is between 200° C. and 600° C. and the second temperature is between 10° C. and 200° C.

DETAILED DESCRIPTION

Figure 1:
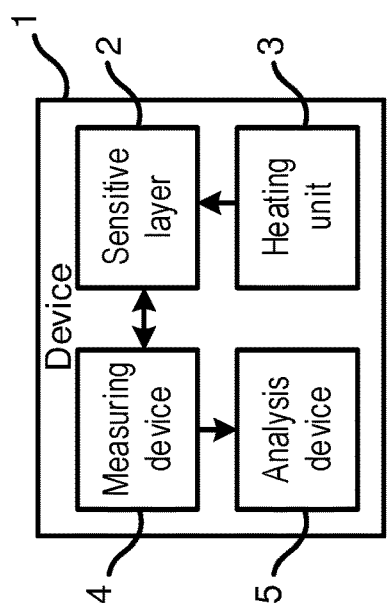
FIG. 1 is a block diagram of a device for analyzing a gas, according to an example embodiment of the present invention.

A block diagram of a device 1 for analyzing a gas is illustrated in FIG. 1. Device 1 is a sensor element or sensor chip, including a metal oxide-containing conductive sensitive layer or (semi)conductor layer. The sensitive layer can, for example, include at least one material of tin oxide (SnOx), SnO, or an arbitrary mixture of SnO and SnO2, tungsten oxide, zinc oxide, or titanium oxide. The electrical conductivity and, as a result, the electrical resistance of sensitive layer 2 is a function of the type and of the concentration of components of a surrounding gas.

Device 1 further includes a heating unit 3 that is designed to heat sensitive layer 2. Heating unit 3 heats sensitive layer 2 initially to a first temperature T1 that is between 200° C. and 600° C. and preferably between 300° C. and 400° C. Sensitive layer 2 is then maintained for a first predefined time period D1 at first temperature T1. The first predefined time period is preferably between a millisecond and 10 seconds. A certain deviation from first temperature T1 can also be tolerable, for example, a deviation of 1° C., 5° C., 10° C., 20° C., or 50° C.

Heating unit 3 subsequently reduces the temperature of sensitive layer 2 to a second temperature T2 that is preferably between 10° C. and 150° C. and particularly preferably between 70° C. and 150° C. A reduction of the temperature is understood within the meaning of the present invention to mean that the heating power of heating unit 3 is reduced. Sensitive layer 2 is thus heated less intensively, so that its temperature is reduced relative to first temperature T1. Heating unit 3 maintains sensitive layer 2 in turn for a second predefined time period D2 at second temperature T2. A deviation from second temperature T2 is again tolerable within the limits indicated above.

Heating unit 3 subsequently increases the temperature of sensitive layer 2 in turn to a third temperature T3 and maintains sensitive layer 2 for a predefined third time period D3 at third temperature T3. Third temperature T3 is preferably as high as first temperature T1, but can also deviate from first temperature T1. Third temperature T3 is above the stability range of the adsorbate to be investigated or of the near-surface chemical compound. Temperature T3 can be designed as a function of the concentration to be checked and of the measuring electronics. A preferably high temperature results in a more rapid decomposition, but requires a higher time resolution. Conversely, the temperature should not be too low in order to shift the conductivity into the desired measuring range by increasing the temperature.

Device 1 further includes a measuring unit 4 that is designed to measure the electrical resistance of sensitive layer 2. For this purpose, measuring unit 4 measures at least one resistance value, preferably, however, a multitude of resistance values. The first measurement of the resistance is carried out after a predefined time period after the increase to third temperature T3, preferably in a time range between 2 millisecond and 2 seconds after the temperature increase.

The device includes an analysis device 5 that is designed to analyze the composition of the gas based on the measured at least one electrical resistance value. According to an example embodiment, measuring device 4 detects for this purpose a comparison measured value already during the first phase, during which sensitive layer 2 is heated to first temperature T1. By comparing the measured electrical resistance values with the comparison measured value, it is possible to determine the change of the electrical resistance based on the adsorption at second temperature T2. Analysis device 5 is designed to determine the presence and/or concentration of components in the gas based on this comparison.

Figure 2:
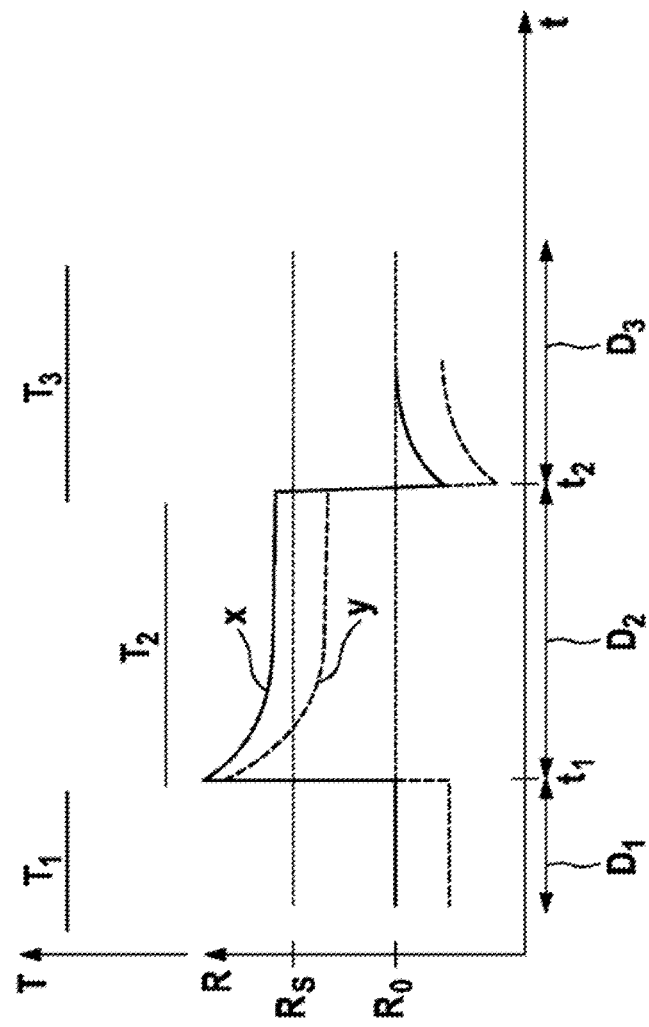
FIG. 2 illustrates a chronological profile of the electrical resistance of a sensitive layer for various concentrations, according to an example embodiment of the present invention.

An exemplary chronological profile of temperature T and of electrical resistance R of sensitive layer 2 is illustrated in FIG. 2. Temperature T1 of sensitive layer 2 during first predefined time period D1 corresponds to temperature T3 during third predefined time period D3. Temperature T2 is reduced during an intervening second predefined time period D2.

Once the temperature is reduced to a first point in time t1, resistance R increases drastically as a result of the temperature. Due to the adsorption incipient at lower temperature T2, the resistance continually decreases and approaches an asymptotic value.

With the subsequent renewed increase of the temperature to a second point in time t2 to third temperature T3, the resistance drops to a value that is lower than value R0 due to the adsorbed substances during first predefined time period D1, but asymptotically approaches this value again due to the desorption.

The respective profile of resistance R for two different concentrations of particular sulfurous substances is illustrated in FIG. 2. A high concentration Y results overall in lower resistance values as well as a stronger drop of the resistance during second predefined time period D2 as compared to a lower concentration X. Analysis device 5 is thus able itself to determine concentrations based on the resistance values detected during third time period D3, either by comparison with the original resistance values or based already on the absolute values.

As is apparent from FIG. 2, resistance R is above the measuring threshold RS of measuring device 4 during second time period D2 at least for a certain time period and, in particular, for low concentrations X. During third time period D3, however, the resistance values are again far below measuring threshold RS, so that a measurement of the resistance values can be easily carried out.

Figure 3:
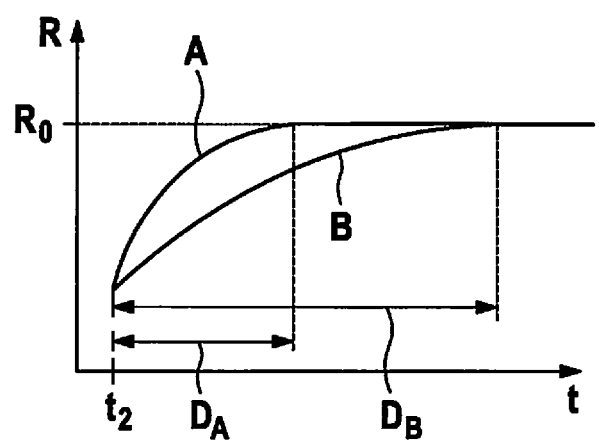
FIG. 3 illustrates a chronological profile of the electrical resistance of a sensitive layer for various substances, according to an example embodiment of the present invention.

As shown in FIG. 3, the exact profile of resistance R at third temperature T3 is also a function of the chemical composition of the gas. Thus, the resistance value for organic compounds A reaches essentially the asymptotic resistance value R0 already after a decay period DA of approximately one second, whereas the corresponding decay period DB for sulfur compounds B is in the range of approximately 10 seconds and, thus, significantly higher, since sulfur compounds desorb more slowly than organic compounds. By determining the profile of the resistance value, analysis device 5 is thus able to distinguish between different chemical substances. Analysis device 5 is able, in particular, to distinguish sulfur compounds from organic compounds taking the decay period into consideration.

The gas to be investigated can be located around sensitive layer 2 during the entire method process. According to an example embodiment, however, the gas is located in the surroundings of sensitive layer 2 solely during the reduction of the temperature to second temperature T2. This is normally sufficient, since it is merely in this time period that the components of the gas adsorb. Second predefined time period D2 is then predefined by the availability of the gas to be checked and can be limited approximately to the duration of an exhalation process of several seconds. Thus, analysis device 5 ascertains the composition of the gas during second predefined time period D2. Alternatively, however, the gas can also be collected and stored.

According to an example embodiment of the present invention, multiple measured values at third temperature T3 can be stored in a characteristic map. For example, measured values having an amplified transient signal as well as further measured values can be stored, in which the development of the stationary value is to be disregarded. In this way, it is possible to ascertain both the concentrations of both sulfurous compounds as well as of organic compounds. The measured values and the characteristic map can also include measured values during first temperature T1.

The method can preferably be carried out repeatedly. In the event the first temperature corresponds to the third temperature, a change need merely take place between two different temperatures. The end time of one measurement corresponds at the same time to the initial state of the next measurement.

What is claimed is:

1. A method for analyzing a gas, the method comprising:
   measuring at least one value of an electrical resistance of a sensitive metal oxide-containing layer that is exposed to the gas, the measuring being performed while a temperature of the sensitive metal oxide-containing layer is a first temperature;
   reducing the temperature of the sensitive metal oxide-containing layer from the first temperature to a second temperature, the temperature of the sensitive metal oxide-containing layer being maintained at the second temperature for a predetermined time period;
   subsequent to the reduction, increasing the temperature of the sensitive metal oxide-containing layer to a third temperature;
   measuring at least two values of the electrical resistance of the sensitive metal oxide-containing layer while the sensitive metal oxide-containing layer is at the third temperature;
   and analyzing components of the gas based on a comparison of the measured at least one value of the electrical resistance at the first temperature with the at least two values of the electrical resistance at the third temperature.

2. The method of claim 1, further comprising ascertaining a chronological profile of the electrical resistance, wherein the analysis is additionally based on the chronological profile of the electrical resistance.

3. The method of claim 2, further comprising determining, based on the chronological profile, a presence and/or concentration in the gas of sulfur compounds, organic compounds, and/or carbon monoxide.

4. The method of claim 1, wherein the third temperature is the same as the first temperature.

5. The method of claim 1, wherein a time required for the temperature reduction is negligible relative to the predetermined time period during which the sensitive layer is maintained at the second temperature and/or to a predetermined time period during which the sensitive metal oxide-containing layer is maintained at the third temperature.

6. The method of claim 1, wherein the measuring of a first value of the electrical resistance while the sensitive metal oxide-containing layer is at the third temperature takes place in a time period of between 2 milliseconds and 2 seconds after the increasing of the temperature of the sensitive metal oxide-containing layer to the third temperature.

7. The method of claim 1, wherein the first temperature and the third temperature are between 200° C. and 600° C., and the second temperature is between 10° C. and 200° C.

8. A device comprising:
a temperature controller;
a sensor; and
a processor;
wherein the device is configured to perform a method for analyzing a gas, the method comprising:
the sensor measuring at least one value of an electrical resistance of a sensitive metal oxide-containing layer that is exposed to the gas, the measuring being performed while a temperature of the sensitive metal oxide-containing layer is a first temperature;
the temperature controller reducing the temperature of the sensitive metal oxide-containing layer from the first temperature to a second temperature, the temperature of the sensitive metal oxide-containing layer being maintained by the temperature controller at the second temperature for a predetermined time period;
subsequent to the reduction, the temperature controller increasing the temperature of the sensitive metal oxide-containing layer to a third temperature;
the sensor measuring at least two values of the electrical resistance of the sensitive metal oxide-containing layer while the sensitive layer is at the third temperature; and
the processor analyzing components of the gas based on a comparison of the measured at least one value of the electrical resistance at the first temperature with the at least two values of the electrical resistance at the third temperature.

9. The device of claim 8, further comprising the sensitive metal oxide-containing layer.

10. The device of claim 8, wherein the temperature controller is a heater.

* * * * *